US010329396B2

(12) United States Patent
Kale et al.

(10) Patent No.: US 10,329,396 B2
(45) Date of Patent: Jun. 25, 2019

(54) PROCESS FOR IMMOBILIZING ONE OR MORE RECEPTOR BIOMOLECULES ON ONE OR MORE SOLID SURFACES

(71) Applicant: Nanosniff Technologies Pvt. Ltd., Mumbai (IN)

(72) Inventors: Nitin Kale, Mumbai (IN); Sumona Dhara, Thane (IN); Dadasaheb Sangave, Solapur (IN); Kapil Bardeja, Greater Noida (IN)

(*) Notice: Subject to any disclaimer, the term of this patent is extended or adjusted under 35 U.S.C. 154(b) by 0 days.

(21) Appl. No.: 15/742,027

(22) PCT Filed: Jul. 12, 2016

(86) PCT No.: PCT/IN2016/050234
§ 371 (c)(1),
(2) Date: Jan. 4, 2018

(87) PCT Pub. No.: WO2017/009869
PCT Pub. Date: Jan. 19, 2017

(65) Prior Publication Data
US 2018/0194914 A1    Jul. 12, 2018

(30) Foreign Application Priority Data
Jul. 14, 2015 (IN) .......................... 2662/MUM/2015

(51) Int. Cl.
*C08J 7/12* (2006.01)
*G01N 33/487* (2006.01)
(Continued)

(52) U.S. Cl.
CPC ........... *C08J 7/12* (2013.01); *A61K 39/39533* (2013.01); *C07K 16/18* (2013.01);
(Continued)

(58) Field of Classification Search
None
See application file for complete search history.

(56) References Cited

U.S. PATENT DOCUMENTS 4,746,553 A * 5/1988 Crisafulli .............. B05C 5/0208
118/305
6,395,326 B1 * 5/2002 Castro ..................... A61L 31/10
427/2.24
(Continued)

FOREIGN PATENT DOCUMENTS

WO    WO-9850773 A2 * 11/1998 ............... G01G 3/13
WO    WO-2009066275 A1 * 5/2009 ....... G01N 33/54353
(Continued)

OTHER PUBLICATIONS

Xiong et al. Channel specific coatings on microfabricated chips. Journal of Chromatography, 924, pp. 165-176. 2001 (Year: 2001).*
(Continued)

*Primary Examiner* — Cachet I Sellman

(57) ABSTRACT

An asymmetric immobilization process that immobilizes a one or more receptor biomolecules on one or more solid surfaces is provided. The asymmetric immobilization process includes the following steps: (i) activating the one or more solid surfaces using an oxidizing agent; (ii) treating the one or more solid surfaces with aminosilane to obtain a one or more amine functionalized solid surfaces; (iii) treating the one or more receptor biomolecules with a 1-Ethyl-3-(3-dimethylaminopropyl)carbodiimide (EDC) to obtain a one or more site-specific EDC activated receptor biomolecules; and (iv) immobilizing the one or more site-specific EDC activated receptor biomolecules on a first layer of the one or more amine functionalized solid surfaces, wherein the immobilizing comprises treating the one or more site-specific EDC activated receptor biomolecules with amine groups of the first layer of the one or more amine functionalized solid surfaces to form a covalent amide bond.

4 Claims, 10 Drawing Sheets

(51) Int. Cl.
*A61K 39/395* (2006.01)
*C07K 16/18* (2006.01)
*G01N 33/543* (2006.01)
*C08G 77/388* (2006.01)
*C08L 23/06* (2006.01)
*C08L 25/06* (2006.01)
*C08L 27/06* (2006.01)
*C08L 33/12* (2006.01)

(52) U.S. Cl.
CPC . *G01N 33/48728* (2013.01); *G01N 33/48785* (2013.01); *G01N 33/54353* (2013.01); *G01N 33/54373* (2013.01); *G01N 33/54393* (2013.01); *C08G 77/388* (2013.01); *C08L 23/06* (2013.01); *C08L 25/06* (2013.01); *C08L 27/06* (2013.01); *C08L 33/12* (2013.01)

(56) References Cited

U.S. PATENT DOCUMENTS

| | | | |
|---|---|---|---|
| 6,699,719 B2* | 3/2004 | Yamazaki | B01J 19/0046 422/82.02 |
| 8,197,879 B2* | 6/2012 | Fox | A61F 2/07 427/2.1 |
| 8,635,711 B1* | 1/2014 | Evans | G01Q 60/42 850/1 |
| 2004/0028804 A1* | 2/2004 | Anderson | B01J 19/0046 506/32 |
| 2005/0233062 A1* | 10/2005 | Hossainy | A61F 2/82 427/2.1 |
| 2008/0160638 A1* | 7/2008 | Lederman | G01N 33/54373 436/525 |
| 2013/0233729 A1* | 9/2013 | Choi | G01N 27/403 205/786 |
| 2016/0280723 A1* | 9/2016 | Zhang | C07F 7/10 |

FOREIGN PATENT DOCUMENTS

| | | | | |
|---|---|---|---|---|
| WO | WO-2010044083 A2 * | 4/2010 | | B01L 3/50857 |
| WO | WO-2014056896 A3 * | 7/2014 | | C07K 14/415 |

OTHER PUBLICATIONS

Bietsch et al. Rapid functionalization of cantilever array sensors by inkjet printing. Nanotechnology 15 pp. 873-990. 2004 (Year: 2004).*

Xia et al. A simple method for covalent immobilization of proteins on porous silicon surfaces. Chemistry Letters. vol. 34 No. 2.2005 pp. 226-227 (Year: 2005).*

* cited by examiner

PROCESS FOR IMMOBILIZING ONE OR MORE RECEPTOR BIOMOLECULES ON ONE OR MORE SOLID SURFACES

BACKGROUND

Technical Field

The embodiments herein generally relate to a process of immobilizing one or more receptor biomolecules on one or more solid surfaces, and, more particularly, to a process for immobilizing one or more antibodies on one or more microcantilevers.

Description of the Related Art

Many experimental approaches in biology, and applications in diagnostics and industrial sensing require bioreceptors to be immobilized on solid surfaces (e.g., micro-cantilevers). For which, the inert substrate requires functional groups which provide the necessary chemistry for bioreceptor binding. However, achieving asymmetric and covalent immobilization of bioreceptors on the solid surface, or onto one surface (i.e., either upper or lower surface) of a suspended solid surface is critical. Recent introduction of bioreceptors in Bio-Microelectromechanical (MEMS) systems require the bioreceptors to be immobilized in a distinctive pattern on the device/solid surfaces. To prevent the unnecessary adsorption of bioreceptors throughout the solid surfaces, to avoid both false positive and negative responses in assays, and to avoid large background signals that limits sensitivity of these devices, asymmetric or selective immobilization process is a requisite.

The Bio-Microelectromechanical device is efficient when a comparative analysis of the immobilized surface is carried out with a bare surface. The Bio-Microelectromechanical device is non-reactive which requires a blocking agent that does not denature, or hinder the adjacent bioreceptors activity. The blocking agent should react completely to block the surface functional group of the solid surface to prevent any non-specific binding of an analyte/protein to that solid surface. The process should be rapid, so that, only small amount of bioreceptors are necessary, and the problem of solvent evaporation is minimized. The process should provide control over the density of immobilized bioreceptors, to ease steric interactions of neighboring bioanalytes. The process should ensure that the immobilized bioreceptors are oriented in a site-specific (tail-on-end) fashion, and may render the antigen binding site facing away from the solid surface. Hence, the antigen binding site is only available to antigens/bioanalytes for interaction.

The concept of using immobilized bioreceptors to target bioanalytes has extended beyond chromatographic applications to magnetic particles, latex beads, nanoparticles, macro-beads, membranes, microplates, optical fibers, array surfaces, dipsticks, and a host of other devices that facilitate the capture or detection of specific bioanalytes. Hence, designing a process that covalently links the bioreceptors to the solid surface is necessary. The process may enhance the performance of the solid support in a number of ways. The covalent attachment of the bioreceptors through conjugation chemistry includes easily reactive components such as primary amines, sulfhydryls, aldehydes, and carboxylic acids. However, there needs to be good compatibility between the chemical reagents, and surface chemistry which does not alter or modify the conformation of the bioreceptors.

Additionally, coupling of the surface chemistry functional groups to amine terminal, or carboxyl terminal of the antibodies is used for obtaining a stable, covalent immobilization procedure. The N-terminus present in the polypeptide chain (called the alpha-amine), and in the side chain of lysine (Lys, K) residues (called the epsilon-amine) are the most common functional targets for immobilizing protein molecules. For amine coupling, crosslinkers such as Glutaraldehyde are used for protein immobilization which shows cross-linking with the reactive species of biomolecule results into aldol condensation or Michael-type addition. As a result, there are discrepancies about the main reactive species that participate in the cross-linking with gultaraldehyde. Further use of Glutaraldehyde, as crosslinkers, may cause precipitation of antibody/bioreceptors, irregular distribution and randomized orientation. The second most common functional target of antibodies is the carboxylic acid groups at the C-terminal position and within the side chains of aspartic acid and glutamic acid. For C-terminal coupling, the common surface chemistry functionalization include N-hydroxysuccinimide (NHS) coupled with EDC to improve the efficiency of the reaction. However, N-hydroxysuccinimide intermediate undergoes crystallization effects under high ionic strength buffer, and is therefore used to create dry stable amine reactive intermediates (using low ionic buffers). Hence, reactions involving slightly alkaline buffer like PBS (pH 7-9) may cause crystallization of NHS. Further a humid/sultry condition is required for antibody incubation which may account for a disproportionate state of carboxyl-activated antibodies.

WO2014056896 A2 has utilized (3-Aminopropyl)triethoxysilane (APTES) to directly immobilize the antibodies without the use of hetero- or bifunctional cross-linkers (an one-step process of immobilization). However, direct usage of APTES for antibody immobilization on a solid surface may initiate different amide coupling between APTES and antibody, or physical adsorption of antibody to the surface (if the APTES is not uniformly present on the surface). In absence of any cross linkers or EDC, the APTES amine groups become positively charged in mere presence of aqueous solution/water which enables the amine groups of APTES to bind to the anionic carboxylate groups of antibody via electrostatic interactions, which results into weak coupling to the solid surface. Additionally, the silanol groups are capable of displaying intra and inter ionic interactions with the antibody. Therefore, the orientation of bounded antibody might also be affected and thereby reducing their bioanalytical performance. Hence, there remains a need for a zero-length crosslinker which may overcome the above-mentioned issues.

To fully utilize the potential of proteins/bioreceptors in various applications, the key is to immobilize biomolecules on the solid surfaces with particular consideration to oriented immobilization, also referred to as site-specific immobilization, which is believed to improve homogeneous surface covering and accessibility of the active site. Hence, there remains a need for a faster and simpler process which enables improved and more reliable covalent binding between the bioreceptors and the solid surfaces.

SUMMARY

In view of the foregoing, an embodiment herein provides an asymmetric immobilization process that immobilizes one or more receptor biomolecules on one or more solid surfaces. The asymmetric immobilization process includes the following steps: (i) activating the one or more solid surfaces using an oxidizing agent; (ii) treating the one or more solid surfaces with aminosilane to obtain one or more amine functionalized solid surfaces; (iii) treating the one or more receptor biomolecules with a 1-Ethyl-3-(3-dimethylaminopropyl)carbodiimide (EDC) to obtain one or more site-specific EDC activated receptor biomolecules; and (vi) immobilizing the one or more site-specific EDC activated receptor biomolecules on a first layer of the one or more amine functionalized solid surfaces, wherein the immobilizing comprises treating the one or more site-specific EDC activated receptor biomolecules with amine groups of the first layer of the one or more amine functionalized solid surfaces to form a covalent amide bond. In one embodiment, the asymmetric immobilization process includes the step of coating a second layer of the one or more amine functionalized solid surfaces with an amine blocker. In one embodiment, the asymmetric immobilization includes the following steps: (i) washing the one or more amine functionalized solid surfaces using organic solvents after treating the one or more solid surfaces with the aminosilane; (ii) washing the one or more site-specific EDC activated receptor biomolecules that are excess from the one or more amine functionalized solid surfaces using at least one of (a) phosphate buffer saline, (b) de-ionised water after immobilizing the one or more site-specific EDC activated receptor biomolecules on the one or more amine functionalized solid surfaces; and (iii) treating the first layer of the one or more amine functionalized solid surfaces with bovine serum albumin to block unbound amine groups of the one or more amine functionalized solid surfaces.

In yet another embodiment, the EDC is hydrolyzed from the one or more site-specific EDC activated receptor biomolecules when the one or more site-specific EDC activated receptor biomolecules binds with amine groups of the one or more amine functionalized solid surfaces. In yet another embodiment, the one or more receptor biomolecules is selected from a group that includes: (i) an antibody; (ii) a recombinant antibody; (iii) a protein; (iv) an antigen; (v) an enzyme; (vi) a nucleic acid; (vii) an oligonucleotide; (viii) an aptamers; (ix) a fragment of antibody; (x) a micro RNA; (xi) a modified mRNA; and (xii) a camelid.

In yet another embodiment, the one or more solid surfaces is selected from a group that includes: (i) cellulose; (ii) gelatin; (iii) polyvinyl chloride; (iv) polystyrene; (v) polyethylene; (vi) polypropylene; (vii) polyacrylonitrile; (viii) Polyvinyl butyral (PVB); (ix) Cyclic olefin copolymer; (x) Polydimethylsiloxane (PDMS); (xi) Poly(methyl methacrylate) (PMMA); (xii) Polysulfone; (xiii) Polyimide; (xiv) acrylate; (xv) silica; (xvi) glass; (xvii) activated carbon; (xviii) silicon nitride; (xix) silicon nitride; and (xx) gold.

In one aspect, an asymmetric immobilization process that immobilizes one or more receptor biomolecules on one or more micro-cantilevers is provided. The asymmetric immobilization process includes the following steps: (i) activating the one or more micro-cantilevers using an oxidizing agent; (ii) treating the one or more micro-cantilevers with aminosilane to obtain one or more amine functionalized micro-cantilevers; (iii) treating the one or more receptor biomolecules with a 1-Ethyl-3-(3-dimethylaminopropyl) carbodiimide (EDC) to obtain one or more site-specific EDC activated receptor biomolecules; (vi) immobilizing the one or more site-specific EDC activated receptor biomolecules on a first layer of the one or more amine functionalized micro-cantilevers, wherein the immobilizing comprises treating the one or more site-specific EDC activated receptor biomolecules with amine groups of the first layer of the one or more amine functionalized micro-cantilevers to form a covalent amide bond, wherein the EDC is hydrolyzed from the one or more site-specific EDC activated receptor biomolecules when the one or more site-specific EDC activated receptor biomolecules binds with amine groups of the one or more amine functionalized micro-cantilevers; (v) coating a second layer of the one or more amine functionalized micro-cantilevers with at least one of (a) acyl chloride, and (b) anhydrides; and (vi) treating the first layer of the one or more amine functionalized micro-cantilevers with bovine serum albumin to block unbound amine groups of the one or more amine functionalized micro-cantilevers. In one embodiment, the acyl chloride is selected from a group that includes: (i) formyl chloride (CHClO); (ii) ethanoyl chloride (C2H3ClO); (iii) propanoyl chloride (C3H5ClO); (iv) butanoyl chloride (C4H7ClO); and (v) octanoyl chloride (C8H15ClO).

In another aspect, an asymmetric immobilization process that immobilizes one or more receptor biomolecules on one or more micro-cantilevers is provided. The asymmetric immobilization process includes the following steps: (i) activating the one or more micro-cantilevers using an oxidizing agent; (ii) treating the one or more micro-cantilevers with aminosilane to obtain one or more amine functionalized micro-cantilevers; (iii) washing the one or more amine functionalized micro-cantilevers using organic solvents; (iv) treating the one or more receptor biomolecules with a 1-Ethyl-3-(3-dimethylaminopropyl)carbodiimide (EDC) to obtain one or more site-specific EDC activated receptor biomolecules; (v) immobilizing the one or more site-specific EDC activated receptor biomolecules on a first layer of the one or more amine functionalized micro-cantilevers, wherein the immobilizing comprises treating the one or more site-specific EDC activated receptor biomolecules with amine groups of the first layer of the one or more amine functionalized micro-cantilevers to form a covalent amide bond, wherein the EDC is hydrolyzed from the one or more site-specific EDC activated receptor biomolecules when the one or more site-specific EDC activated receptor biomolecules binds with amine groups of the one or more amine functionalized micro-cantilevers; (vi) coating a second layer of the one or more amine functionalized micro-cantilevers with least one of (a) acyl chloride, and (b) anhydrides; (vii) washing the one or more site-specific EDC activated receptor biomolecules that are excess from the one or more amine functionalized micro-cantilevers using at least one of (a) a phosphate buffer saline, (b) de-ionised water; and (viii) treating the first layer of the one or more amine functionalized micro-cantilevers with bovine serum albumin to block unbound amine groups of the one or more amine functionalized micro-cantilevers.

In one embodiment, the one or more receptor biomolecules is selected from a group that includes: (i) an anti-myoglobin antibody; (ii) an anti-FABP3 antibody; (iii) an anti-troponin antibody; (iv) an anti-Human IgG antibody; (v) an anti-IMA Antibody; (vi) an anti-Myeloperoxidase (MPO) Antibody; (vii) an anti-Glycogen Phosphorylase Isoenzyme BB-(GPBB) Antibody; (viii) an anti-Serum creatinine antibody; (ix) an anti-Serum cystatin C antibody; (x) an anti-Urine albumin antibody; (xi) an anti-Neutrophil gelatinase-associated lipocalin (NGAL) antibody; (xii) an anti-Kidney injury molecule 1 (KIM-1) antibody; (xiii) an anti-Liver-type fatty acid-binding protein (L-FABP) antibody; (xiv) an anti-Interleukin 18 (IL-18), β-trace protein (BTP) antibody; (xv) an anti-Aasymmetric dimethylarginine (ADMA) antibody; and (xvi) an anti-Urine cystatin C antibody.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

Figure 1A:
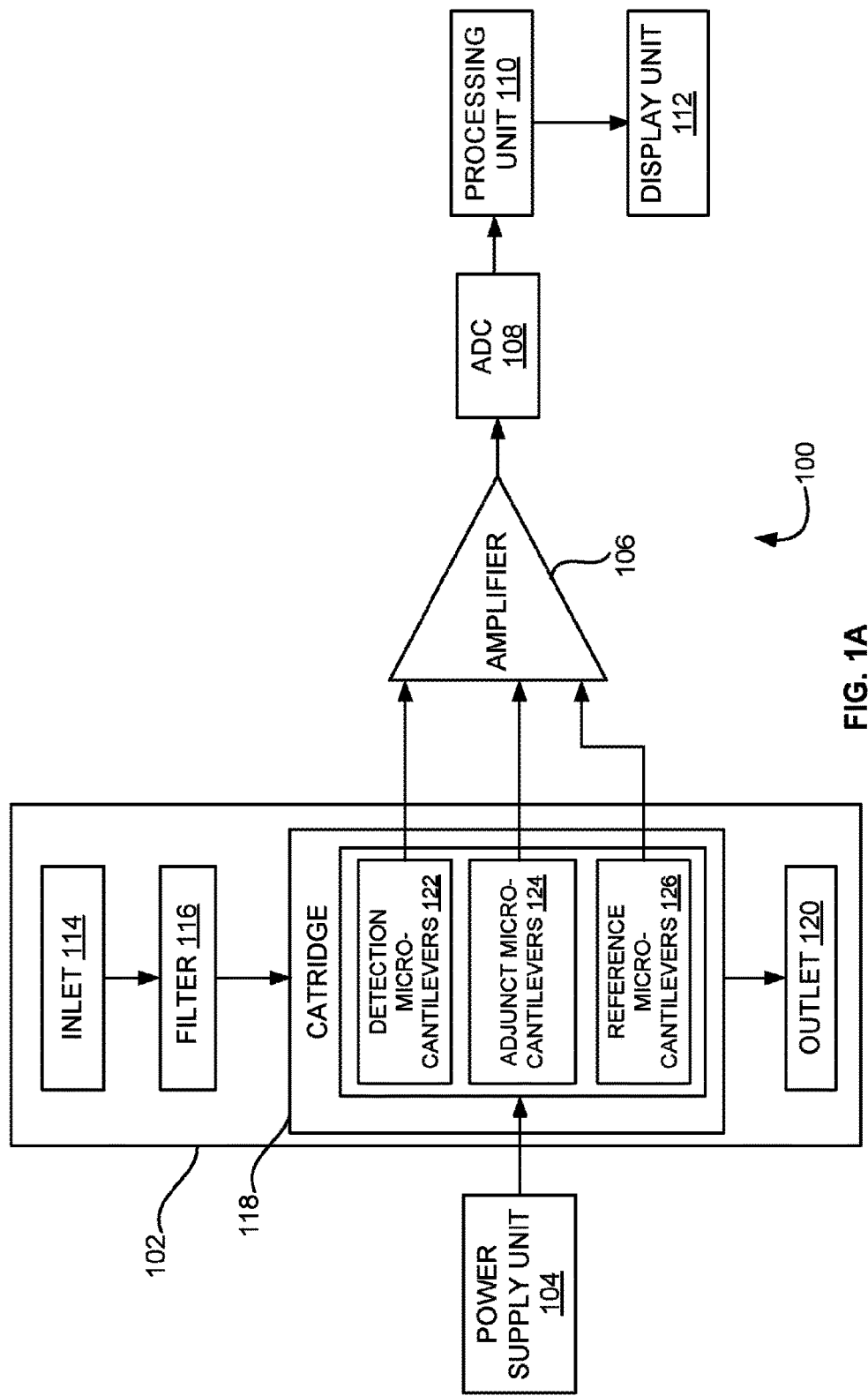
FIG. 1A illustrates a block diagram of a detection system that detects a concentration of an analyte biomolecule in a sample to diagnose a disease according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Various embodiments of the process disclosed herein provide an asymmetric process for immobilizing one or more receptor biomolecules (e.g., antibodies) on one or more solid surfaces (e.g., micro-cantilevers). Referring now to the drawings, and more particularly to FIGS. 1A through 4B, where similar reference characters denote corresponding features consistently throughout the figures, there are shown preferred embodiments.

FIG. 1A illustrates a block diagram of a detection system 100 that detects a concentration of an analyte biomolecule in a sample to diagnose a disease according to an embodiment herein. The detection system 100 includes a microfluidic chamber 102, a power supply unit 104, an amplifier 106, an analog to digital converter (ADC) 108, a processing unit 110, and a display unit 112. The microfluidic chamber 102 includes an inlet 114, a filter 116, a detection unit 118, and an outlet 120. The detection unit 118 includes one or more detection micro-cantilevers 122, one or more adjunct micro-cantilevers 124, and one or more reference micro-cantilevers 126. The inlet 114 is adapted to provide a sample to the detection unit 118. The filter 116 is configured to filter the sample to obtain a concentrated sample. In one embodiment, the inlet 114 includes the filter 116 to filter the sample to obtain the concentrated sample. In another embodiment, the microfluidic chamber 102 provides a proper flow of the sample to the detection unit 118 (i.e. one or more detection micro-cantilevers 122, one or more adjunct micro-cantilevers 124, and one or more reference micro-cantilevers 126). The detection unit 118 receives the concentrated sample from the filter 116. The one or more detection micro-cantilevers 122 include a first layer (i.e. an immobilization layer), and a second layer (i.e. a structural layer). The first layer of the one or more detection micro-cantilevers 122 is adapted to be immobilized with one or more first receptor biomolecules (e.g., diagnostic receptor biomolecules, antibodies, enzymes, etc.) using an asymmetric, site-specific, covalent and uniform immobilization process. The one or more adjunct micro-cantilevers 124 include a first layer (i.e. an immobilization layer), and a second layer (i.e. a structural layer). The first layer of the one or more adjunct micro-cantilevers 124 is adapted to be immobilized with one or more second receptor biomolecules (e.g., prognostic and/or surrogate receptor biomolecules, antibodies, enzymes, etc.) using the asymmetric, site-specific, covalent and uniform immobilization process. The second layer of (a) the one or more detection micro-cantilevers 122, and (b) the one or more adjunct micro-cantilevers 124 are adapted to be coated with an amine blocker.

The one or more reference micro-cantilevers 126 include a first layer, and a second layer. The first layer and the second layer of the one or more reference micro-cantilevers 126 are adapted to be coated with the amine blocker. In one embodiment, the amine blocker may be an acid/acyl chloride, or anhydride. The acid chloride may be selected from at least one of (i) formyl chloride (CHClO), (ii) ethanoyl chloride ($C_2H_3ClO$), (iii) propanoyl chloride ($C_3H_5ClO$), (iv) butanoyl chloride ($C_4H_7ClO$), and (v) octanoyl chloride ($C_8H_{15}ClO$), etc. The solvent used for acid/acyl chloride may be chloroform or Dimethylformamide (DMF). The anhydride may be selected from at least one of (i) formic anhydride, (ii) ethanoic anhydride, (iii) propanoic anhydride, (iv) hexanoic anhydride, and (v) nonanoic anhydride, etc.

The one or more detection micro-cantilevers 122, the one or more adjunct micro-cantilevers 124, and the one or more reference micro-cantilevers 126 are adapted to be (i) supplied with a constant current, and (ii) exposed to the concentrated sample. In one embodiment, the one or more detection micro-cantilevers 122, the one or more adjunct micro-cantilevers 124, and the one or more reference micro-cantilevers 126 are pre-calibrated using calibrant solution. In another embodiment, the first layer, and the second layer of (i) the one or more detection micro-cantilevers 122, (ii) the one or more adjunct micro-cantilevers 124, and (iii) the one or more reference micro-cantilevers 126 may be an immobilization layer, and a structural layer respectively. In another embodiment, the first layer (i.e. the immobilization layer), and the second layer (i.e. the structural layer) of (i) the one or more detection micro-cantilevers 122, (ii) the one or more adjunct micro-cantilevers 124, and (iii) the one or more reference micro-cantilevers 126 are made up of dielectric material. In yet another embodiment, (i) the one or more detection micro-cantilevers 122, (ii) the one or more adjunct micro-cantilevers 124, and (iii) the one or more reference micro-cantilevers 126 may include a solid surface. The solid surface may be at least one of (a) natural polymers (i.e. cellulose, gelatin, etc), (b) synthetic polymers (e.g., polyvinyl chloride (PVC or vinyl)), (c) polystyrene, (d) polyethylene, (e) polypropylene, (f) polyacrylonitrile, (g) PVB, (h) silicone, (i) Cyclic olefin copolymer, (j) Polydimethylsiloxane (PDMS), (k) Poly(methyl methacrylate) (PMMA), (l) Polysulfone, (m) Polyimide, (n) acrylate, and (o) inorganic supports (e.g., silica, glass, silicon oxide, silicon nitride, gold, activated carbon).

The one or more detection micro-cantilevers 122, the one or more adjunct micro-cantilevers 124, and the one or more reference micro-cantilevers 126 include one or more piezo-resistive layers. The one or more piezo-resistive layers is embedded in between each of the immobilization layer (i.e. the first layer), and the structural layer (i.e. the second layer) of (a) the one or more detection micro-cantilevers 122, (b) the one or more adjunct micro-cantilevers 124, and (c) the one or more reference micro-cantilevers 126. The detection unit 118 is adapted to measure a change in surface stress of the one or more piezo-resistive layers of at least one of (a) the one or more detection micro-cantilevers 122, and (b) the one or more adjunct micro-cantilevers 124 due to binding of an analyte biomolecule (e.g., antigens, proteins, biomarkers, etc.) with at least one of (i) the one or more first receptor biomolecules (e.g., diagnostic receptor biomolecules), and (ii) the one or more second receptor biomolecules (e.g., prognostic and/or surrogate receptor biomolecules). In one embodiment, the one or more detection micro-cantilevers 122, and the one or more adjunct micro-cantilevers 124 bend either upward or downward when the surface stress of the one or more piezo-resistive layers change due to binding of the analyte biomolecule (e.g., antigens, proteins, etc.) with at least one of (i) the one or more first receptor biomolecules (e.g., diagnostic receptor biomolecules), and (ii) the one or more second receptor biomolecules (e.g., prognostic and/or surrogate receptor biomolecules).

The detection unit 118 is adapted to calculate a change in the resistance of at least one of (a) the one or more detection micro-cantilevers 122, and (b) the one or more adjunct micro-cantilevers 124 due to the change in surface stress of the one or more piezo-resistive layers of at least one of (a) the one or more detection micro-cantilevers 122, and (b) the one or more adjunct micro-cantilevers 124. In one embodiment, the detection unit 118 includes a digital potentiometer to calculate an equivalent resistance of at least one of (a) the one or more detection micro-cantilevers 122, and (b) the one or more adjunct micro-cantilevers 124, and (c) the one or more reference micro-cantilevers 126. In another embodiment, the digital potentiometer is adapted to be supplied with a constant current.

The detection unit 118 is adapted to calculate a change in voltage across (i) at least one of (a) the one or more detection micro-cantilevers 122, and (b) the one or more adjunct micro-cantilevers 124 based on the change in the resistance of at least one of (a) the one or more detection micro-cantilevers 122, and (b) the one or more adjunct micro-cantilevers 124, and (ii) the one or more reference micro-cantilevers 126. The detection unit 118 is further adapted to calculate voltages across the digital potentiometer based on the equivalent resistance of (a) the one or more detection micro-cantilevers 122, (b) the one or more adjunct micro-cantilevers 124, and (c) the one or more reference micro-cantilevers 126.

The amplifier 106 is configured to receive the voltages that corresponds to (i) at least one of (a) the one or more detection micro-cantilevers 122, and (b) the one or more adjunct micro-cantilevers 124, and (c) the one or more reference micro-cantilevers 126, and (ii) the digital potentiometer. The amplifier 106 is configured to subtract the voltages that are received from at least one of (a) the one or more detection micro-cantilevers 122, (b) the one or more adjunct micro-cantilevers 124, and (c) the one or more reference micro-cantilevers 126 with the voltages received from the digital potentiometer to calculate one or more differential voltages. The amplifier 106 is configured to amplify the one or more differential voltage to obtain one or more amplified differential voltages. In one embodiment, the amplifier 106 may be a differential amplifier. The analog to digital converter (ADC) 108 is adapted to convert the one or more amplified differential voltages into a digital signal.

The processing unit 110 is configured to process the digital signal received from the ADC 108 to detect a concentration of the analyte biomolecule (e.g., antigens, proteins, biomarkers, etc.) in the concentrated sample. The processing unit 110 is configured to compare the concentration of the analyte biomolecule that corresponds to at least one of (i) the one or more first receptor biomolecules and (ii) the one or more second receptor biomolecules with a threshold value to diagnose a disease. In one embodiment, the processing unit 110 determines the constant current that is supplied to (a) the one or more detection micro-cantilevers 122, (b) the one or more adjunct micro-cantilevers 124, (c) the one or more reference micro-cantilevers 126, and (d) the digital potentiometer based on (a) a magnitude of the constant current required to detect and measure changes in surface activity and (b) minimizing power dissipation. The constant current may range between 10 nanoamperes and 700 nanoamperes. The detection system 100 may include a display unit that is configured to display a status of one of (a) a disease is diagnosed, (b) no disease is diagnosed, or (c) the concentration of the analyte biomolecule.

In one embodiment, the one or more first receptor biomolecules (e.g., diagnostic receptor biomolecules), and the one or more second receptor biomolecules (e.g., prognostic and/or surrogate receptor biomolecules) are selected from at least one of (i) an antibody, (ii) a recombinant antibody, (iii) a protein, (iv) an antigen, (v) an enzyme, (vi) a nucleic acid, (vii) an oligonucleotide, (viii) an aptamers, (ix) a fragment of antibody, (x) a micro RNA, (xi) a modified mRNA, and (xii) a camelid. In another embodiment, the one or more first receptor biomolecules, and the one or more second receptor biomolecules are selected from at least one (i) an anti-myoglobin antibody, (ii) an anti-FABP3 antibody, (iii) an anti-troponin antibody (e.g., Troponin I, Troponin T, and Troponin C), (iv) an anti-Human IgG antibody, (v) an anti-IMA Antibody, (vi) an anti-Myeloperoxidase (MPO) Antibody, and (vii) an anti-Glycogen Phosphorylase Isoenzyme BB-(GPBB) Antibody.

In yet another embodiment, the microfluidic chamber 102 electrically isolates the concentrated sample from one or more electrical contact pads of at least one of (a) the one or more detection micro-cantilevers 122, and (b) the one or more adjunct micro-cantilevers 124, and (c) the one or more reference micro-cantilevers 126. The outlet 120 is adapted to collect post-testing sample from the detection unit 118. In one embodiment, the detection system 100 may be used by a qualified nurse/technician at a rural primary healthcare facility, or an ambulance. In another embodiment, the detection system 100 may be integrated with existing healthcare monitoring systems that are used in hospitals/health care centers.

An asymmetric immobilization process for immobilizing the first receptor biomolecules (e.g., diagnostic receptor biomolecules), and the second receptor biomolecules (e.g., prognostic and/or surrogate receptor biomolecules) on the one or more detection micro-cantilevers 122, and the one or more adjunct micro-cantilevers 124 respectively includes the following steps: (i) activating the one or more detection micro-cantilevers 122, and the one or more adjunct micro-cantilevers 124 using an oxidizing agent; (ii) treating the one or more detection micro-cantilevers 122, and the one or more adjunct micro-cantilevers 124 with aminosilane to obtain (a) one or more amine functionalized detection micro-cantilevers 122, and (b) one or more amine functionalized adjunct micro-cantilevers 124; (iii) treating (a) the first receptor biomolecules (e.g., diagnostic receptor biomolecules), and (b) the second receptor biomolecules (e.g., prognostic and/or surrogate receptor biomolecules) with a 1-Ethyl-3-(3-dimethylaminopropyl)carbodiimide (EDC) to obtain (a) a site-specific EDC activated first receptor biomolecules, and (b) a site-specific EDC activated second receptor biomolecules; and (iv) immobilizing (a) the site-specific EDC activated first receptor biomolecules, and (b) the site-specific EDC activated second receptor biomolecules on the first layer of (a) the one or more amine functionalized detection micro-cantilevers 122, and (b) the one or more amine functionalized adjunct micro-cantilevers 124. In one embodiment, the immobilizing step includes (i) treating (a) the site-specific EDC activated first receptor biomolecules, and (b) the site-specific EDC activated second receptor biomolecules with amine groups of (a) the first layer of the one or more amine functionalized detection micro-cantilevers 122, and (b) the first layer of the one or more amine functionalized adjunct micro-cantilevers 124 to form a covalent amide bond. In another embodiment, the 1-Ethyl-3-(3-dimethylaminopropyl)carbodiimide (EDC) is hydrolyzed from (a) the site-specific EDC activated first receptor biomolecules, and (b) the site-specific EDC activated second receptor biomolecules when (a) the site-specific EDC activated first receptor biomolecules, and (b) the site-specific EDC activated second receptor biomolecules bind with amine groups of (a) the one or more amine functionalized detection micro-cantilevers 122, and (b) the one or more amine functionalized adjunct micro-cantilevers 124.

The asymmetric immobilization process further includes the following steps: (i) coating a second layer of (a) the one or more amine functionalized detection micro-cantilevers 122, and (b) the one or more amine functionalized adjunct micro-cantilevers 124 with an amine blocker; (ii) washing (a) the one or more amine functionalized detection micro-cantilevers 122, and (b) the one or more amine functionalized adjunct micro-cantilevers 124 using organic solvents after treating (a) the one or more detection micro-cantilevers 122, and (b) the one or more adjunct micro-cantilevers 124 with the aminosilane; (iii) washing (a) the site-specific EDC activated first receptor biomolecules, and (b) the site-specific EDC activated second receptor biomolecules that are excess from (a) the one or more amine functionalized detection micro-cantilevers 122, and (b) the one or more amine functionalized adjunct micro-cantilevers 124 using at least one of (a) phosphate buffer saline, (b) de-ionised (DI) water after immobilizing (i) the site-specific EDC activated first receptor biomolecules, and (ii) the site-specific EDC activated second receptor biomolecules with (a) the one or more amine functionalized detection micro-cantilevers 122, and (b) the one or more amine functionalized adjunct micro-cantilevers 124; and (iv) treating (a) the one or more amine functionalized detection micro-cantilevers 122, and (b) the one or more amine functionalized adjunct micro-cantilevers 124 with bovine serum albumin to block unbound amine groups of (a) the one or more amine functionalized detection micro-cantilevers 122, and (b) the one or more amine functionalized adjunct micro-cantilevers 124. In one embodiment, the amine blocker may be an acid/acyl chloride, or anhydride.

In one embodiment, the asymmetric immobilization process further includes the following steps: (i) treating the one or more reference micro-cantilevers 126 with aminosilane to obtain one or more amine functionalized reference micro-cantilevers 126; (ii) coating a first layer and second layer of the one or more amine functionalized reference micro-cantilevers 126 with an amine blocker; and (iii) washing the one or more amine functionalized reference micro-cantilevers 126 using organic solvents after treating the one or more reference micro-cantilevers 126 with the aminosilane.

Figure 1B:
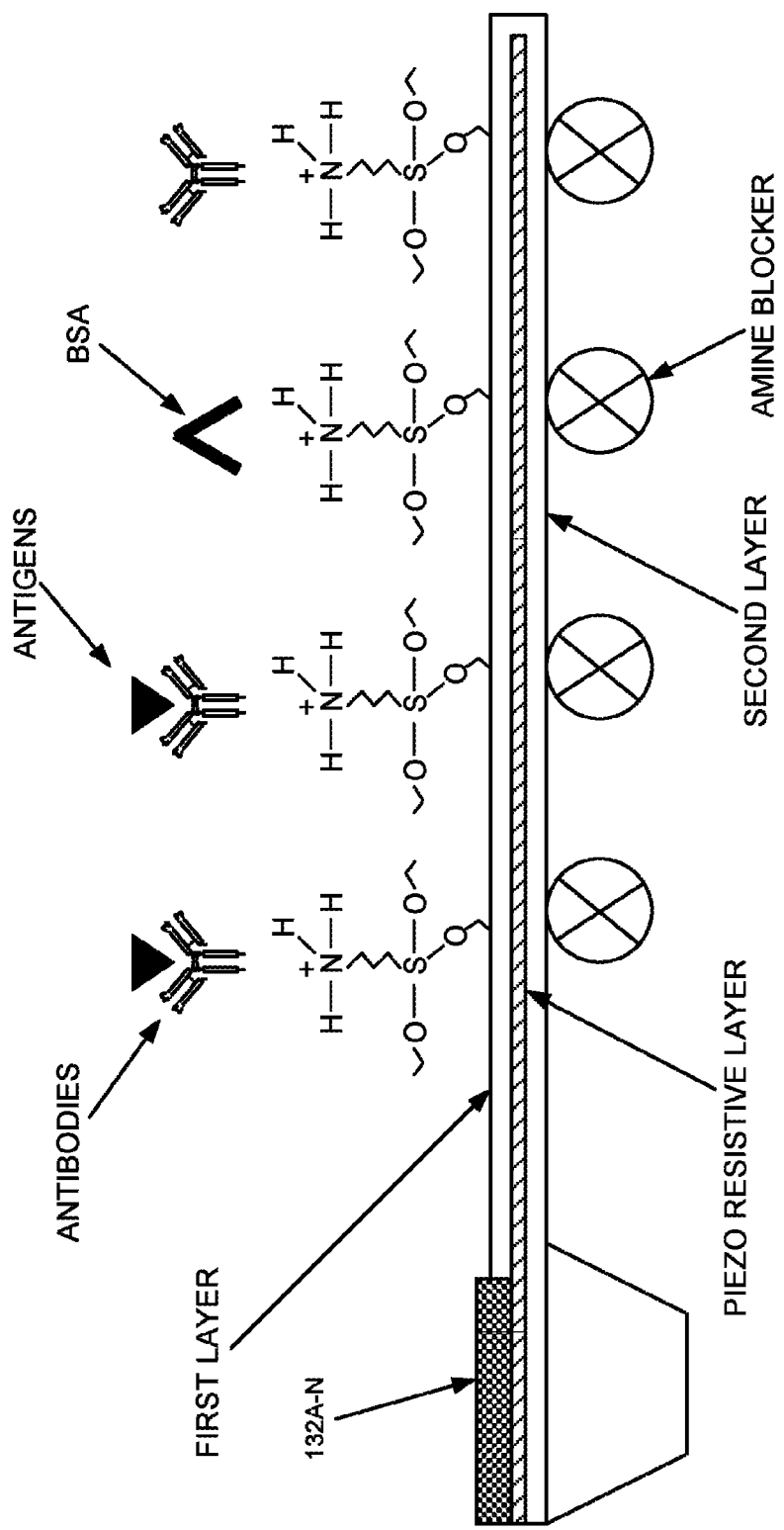
FIG. 1B illustrates an exploded view of layers of (i) one or more detection micro-cantilevers, or (ii) one or more adjunct micro-cantilevers of FIG. 1 according to an embodiment herein.

With reference to FIG. 1A, FIG. 1B illustrates an exploded view of layers of (i) one or more detection micro-cantilevers 122, or (ii) one or more adjunct micro-cantilevers 124 of FIG. 1 according to an embodiment herein. The one or more detection micro-cantilevers 122 include the first layer (i.e. the immobilization layer), and the second layer (i.e. the structural layer). The first layer of the one or more detection micro-cantilevers 122 is adapted to be immobilized with one or more first receptor biomolecules (e.g. antibodies) using an asymmetric, site-specific, covalent and uniform immobilization process. The one or more adjunct micro-cantilevers 124 include the first layer (i.e. the immobilization layer), and the second layer (i.e. the structural layer). The first layer of the one or more adjunct micro-cantilevers 124 is adapted to be immobilized with one or more second receptor biomolecules (e.g., antibodies) using the asymmetric, site-specific, covalent and uniform immobilization process. The second layer of (a) the one or more detection micro-cantilevers 122, and (b) the one or more adjunct micro-cantilevers 124 are adapted to be coated with an amine blocker. In another embodiment, the first layer (i.e. the immobilization layer), and the second layer (i.e. the structural layer) of (i) the one or more detection micro-cantilevers 122, and (ii) the one or more adjunct micro-cantilevers 124 are made up of dielectric material. The one or more electrical contact pads 128A-N to power the one or more detection micro-cantilevers 122, and the one or more adjunct micro-cantilevers 124. The one or more detection micro-cantilevers 122, and the one or more adjunct micro-cantilevers 124 include one or more piezo-resistive layers.

The one or more piezo-resistive layers is embedded in between each of the immobilization layer (i.e. the first layer), and the structural layer (i.e. the second layer) of (a) the one or more detection micro-cantilevers 122, and (b) the one or more adjunct micro-cantilevers 124. The one or more detection micro-cantilevers 122, and the one or more adjunct micro-cantilevers 124 are adapted to be exposed to the concentrated sample. The one or more detection micro-cantilevers 122, and the one or more adjunct micro-cantilevers 124 bend either upward or downward due to binding of the analyte biomolecule (e.g., antigens, proteins, etc.) with at least one of (i) the one or more first receptor biomolecules (e.g., diagnostic receptor biomolecules), and (ii) the one or more second receptor biomolecules (e.g., prognostic and/or surrogate receptor biomolecules). The one or more detection micro-cantilevers 122, and the one or more adjunct micro-cantilevers 124 are treated with bovine serum albumin to block unbound amine groups of the one or more detection micro-cantilevers 122, and the one or more adjunct micro-cantilevers 124.

Figure 2A:
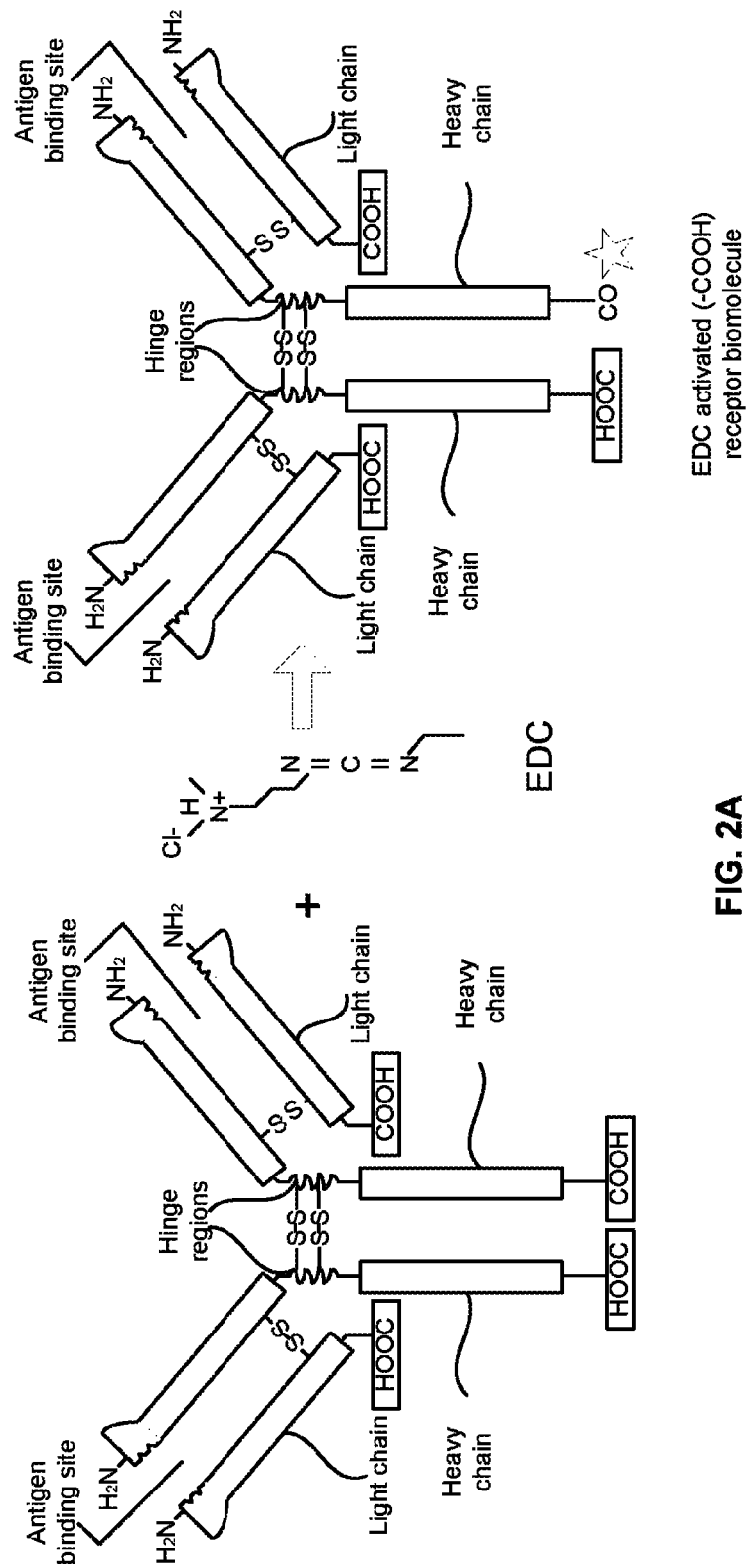
FIG. 2A illustrates a process of treating one or more antibodies with a 1-Ethyl-3-(3-dimethylaminopropyl)carbodiimide (EDC) according to an embodiment herein.

FIG. 2A illustrates a process of treating one or more antibodies with a 1-Ethyl-3-(3-dimethylaminopropyl)carbodiimide (EDC) according to an embodiment herein. The one or more antibodies (e.g., the first receptor biomolecules, or the second receptor biomolecules, etc.) are treated with a 1-Ethyl-3-(3-dimethylaminopropyl)carbodiimide (EDC) to obtain one or more site-specific EDC activated antibodies (e.g., one or more site-specific EDC activated first receptor biomolecules, and one or more site-specific EDC activated second receptor biomolecules). In one embodiment, the EDC is reacted with a C terminal of the one or more antibodies. In another embodiment, the one or more antibodies are selected from at least one of (i) a camelid, (ii) a recombinant antibody, (iii) a protein, (iv) an antigen, (v) an enzyme, (vi) a nucleic acid, (vii) an oligonucleotide, (viii) an aptamers, (ix) a fragment of antibody, (x) a micro RNA, and (xi) a modified mRNA.

Figure 2B:
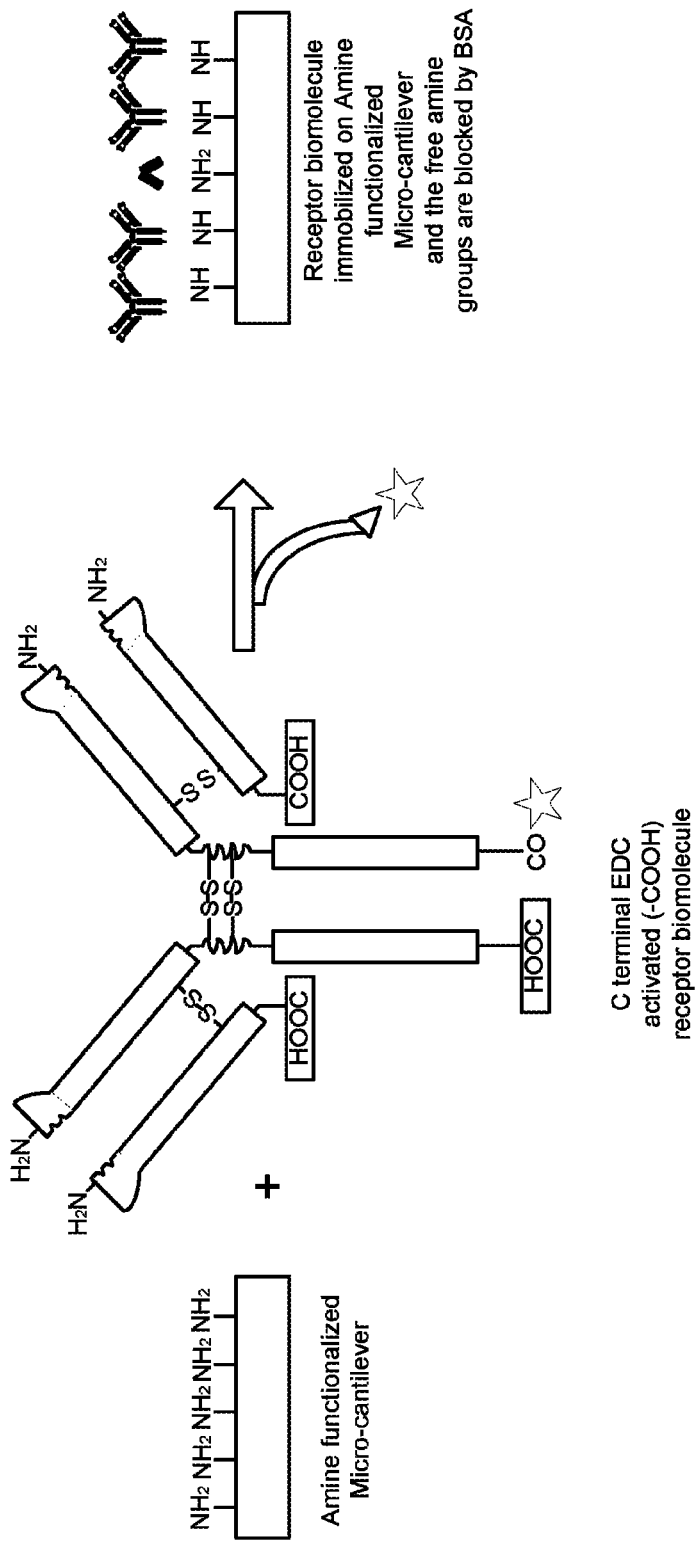
FIG. 2B illustrates a process of immobilizing site-specific EDC activated antibodies on a first layer of one or more micro-cantilevers of FIG. 1 according to an embodiment herein.

With reference to FIG. 2A, FIG. 2B illustrates a process of immobilizing a site-specific EDC activated antibodies on the first layer of one or more micro-cantilevers according to an embodiment herein. The one or more micro-cantilevers (i.e. the one or more detection micro-cantilevers 122, the one or more adjunct micro-cantilevers 124, and the one or more reference micro-cantilevers 126) are activated using an oxidizing agent. In one embodiment, the oxidizing agent is selected from at least one of (i) Oxygen ($O_2$), (ii) Ozone ($O_3$), (iii) Hydrogen peroxide ($H_2O_2$), (iv) Nitric acid ($HNO_3$), (v) Sulfuric acid ($H_2SO_4$), and (vi) Sulphochromic acid, etc. The one or more micro-cantilevers are treated with aminosilane to obtain the one or more amine functionalized micro-cantilevers (i.e. the one or more amine functionalized detection micro-cantilevers 122, the one or more amine functionalized adjunct micro-cantilevers 124, and the one or more amine functionalized reference micro-cantilevers 126). The one or more site-specific EDC activated antibodies are immobilized on the first layer of the one or more amine functionalized micro-cantilevers. In one embodiment, the one or more site-specific EDC activated antibodies are treated with amine groups of the first layer of the one or more amine functionalized micro-cantilevers to form a covalent amide bond. In one embodiment, the 1-Ethyl-3-(3-dimethylaminopropyl)carbodiimide (EDC) is hydrolyzed from the one or more site-specific EDC activated antibodies when the one or more site-specific EDC activated antibodies binds with amine groups of the one or more amine functionalized micro-cantilevers.

Figure 2C:
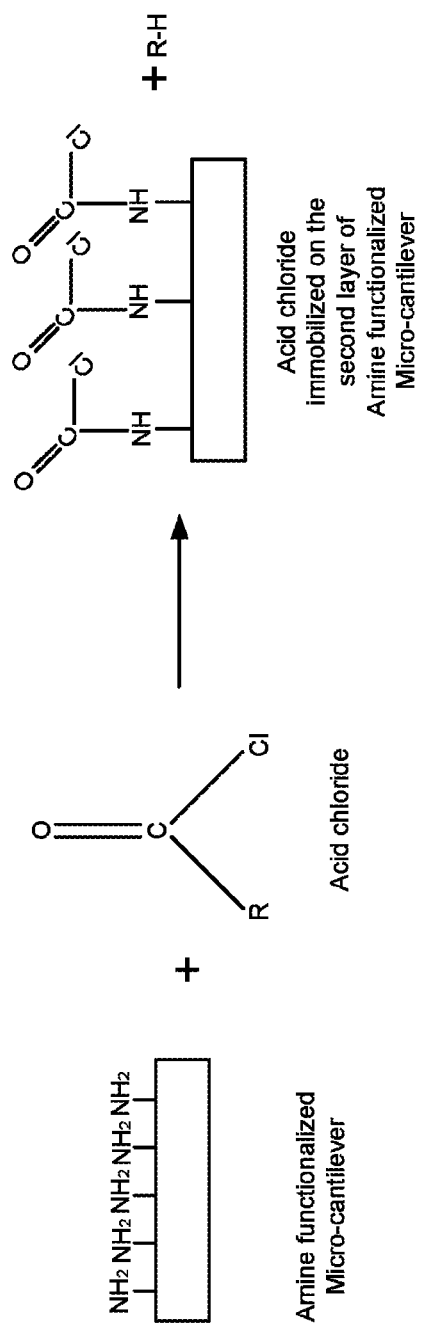
FIG. 2C illustrates a process of coating an amine blocker on a second layer of one or more amine functionalized micro-cantilevers according to an embodiment herein.

With reference to FIGS. 2A and 2B, FIG. 2C illustrates a process of coating the amine blocker on the second layer of one or more amine functionalized micro-cantilevers according to an embodiment herein. The second layer of the one or more amine functionalized micro-cantilevers (i.e. the one or more amine functionalized detection micro-cantilevers 122, the one or more amine functionalized adjunct micro-cantilevers 124, and the one or more amine functionalized reference micro-cantilevers 126) are coated with the amine blocker. In one embodiment, the amine blocker may be an acid/acyl chloride, or anhydride. The acid chloride may be selected from at least one of (i) formyl chloride (CHClO), (ii) ethanoyl chloride ($C_2H_3ClO$), (iii) propanoyl chloride ($C_3H_5ClO$), (iv) butanoyl chloride ($C_4H_7ClO$), and (v) octanoyl chloride ($C_8H_{15}ClO$), etc. The solvent used for acid/acyl chloride may be chloroform or Dimethylformamide (DMF). The anhydride may be selected from at least one of (i) formic anhydride, (ii) ethanoic anhydride, (iii) propanoic anhydride, (iv) hexanoic anhydride, and (v) nonanoic anhydride, etc.

Figure 3A:
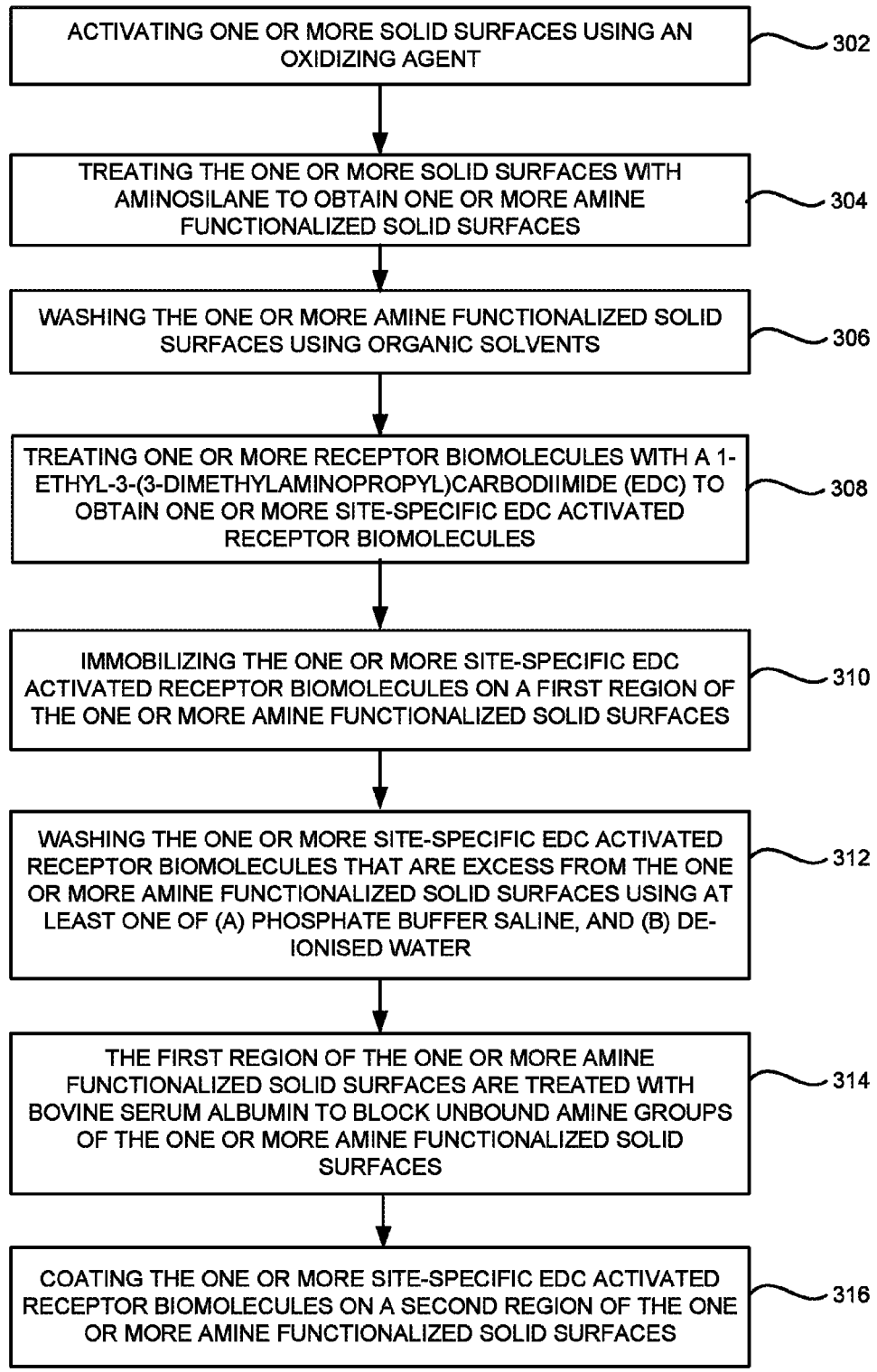
FIG. 3A is a flow diagram illustrating an asymmetric immobilization process of immobilizing one or more receptor biomolecules on one or more solid surfaces according to an embodiment herein.

FIG. 3A is a flow diagram illustrating an asymmetric immobilization process of immobilizing one or more receptor biomolecules on one or more solid surfaces according to an embodiment herein. At step 302, the one or more solid surfaces (i.e. the one or more detection micro-cantilevers 122, the one or more adjunct micro-cantilevers 124, and the one or more reference micro-cantilevers 126) are activated using an oxidizing agent. In one embodiment, the solid surfaces may be at least one of (a) natural polymers (i.e. cellulose, gelatin, etc), (b) synthetic polymers (e.g., polyvinyl chloride (PVC or vinyl)), (c) polystyrene, (d) polyethylene, (e) polypropylene, (f) polyacrylonitrile, (g) PVB, (h) silicone, (i) Cyclic olefin copolymer, (j) Polydimethylsiloxane (PDMS), (k) Poly(methyl methacrylate) (PMMA), (l) Polysulfone, (m) Polyimide, (n) acrylate, and (o) inorganic supports (e.g., silica, glass, silicon oxide, silicon nitride, gold, activated carbon). At step 304, the one or more solid surfaces are treated with aminosilane to obtain the one or more amine functionalized solid surfaces (i.e. the one or more amine functionalized detection micro-cantilevers 122, the one or more amine functionalized adjunct micro-cantilevers 124, and the one or more amine functionalized reference micro-cantilevers 126). At step 306, the one or more amine functionalized solid surfaces are washed using organic solvents. At step 308, the one or more receptor biomolecules (e.g., the one or more first receptor biomolecules, and the one or more second receptor biomolecules) are treated with a 1-Ethyl-3-(3-dimethylaminopropyl)carbodiimide (EDC) to obtain one or more site-specific EDC activated receptor biomolecules (e.g., one or more site-specific EDC activated first receptor biomolecules, and one or more site-specific EDC activated second receptor biomolecules). At step 310, the one or more site-specific EDC activated receptor biomolecules are immobilized on the first region of the one or more amine functionalized solid surfaces (e.g., the one or more amine functionalized detection micro-cantilevers 122, the one or more amine functionalized adjunct micro-cantilevers 124, and the one or more amine functionalized reference micro-cantilevers 126). The one or more site-specific EDC activated receptor biomolecules are treated with amine groups of the first region of the one or more amine functionalized solid surfaces to form a covalent amide bond. In one embodiment, the 1-Ethyl-3-(3-dimethylaminopropyl)carbodiimide (EDC) is hydrolyzed from the one or more site-specific EDC activated receptor biomolecules when the one or more site-specific EDC activated receptor biomolecules bind with amine groups of the one or more amine functionalized solid surfaces.

At step 312, the one or more site-specific EDC activated receptor biomolecules that are excess from the one or more amine functionalized solid surfaces are washed using at least one of (a) phosphate buffer saline, and (b) de-ionised water. At step 314, the first region of the one or more amine functionalized solid surfaces are treated with bovine serum albumin to block unbound amine groups of the one or more amine functionalized solid surfaces. At step 316, a second region of the one or more amine functionalized solid surfaces are coated with the amine blocker.

Figure 3B:
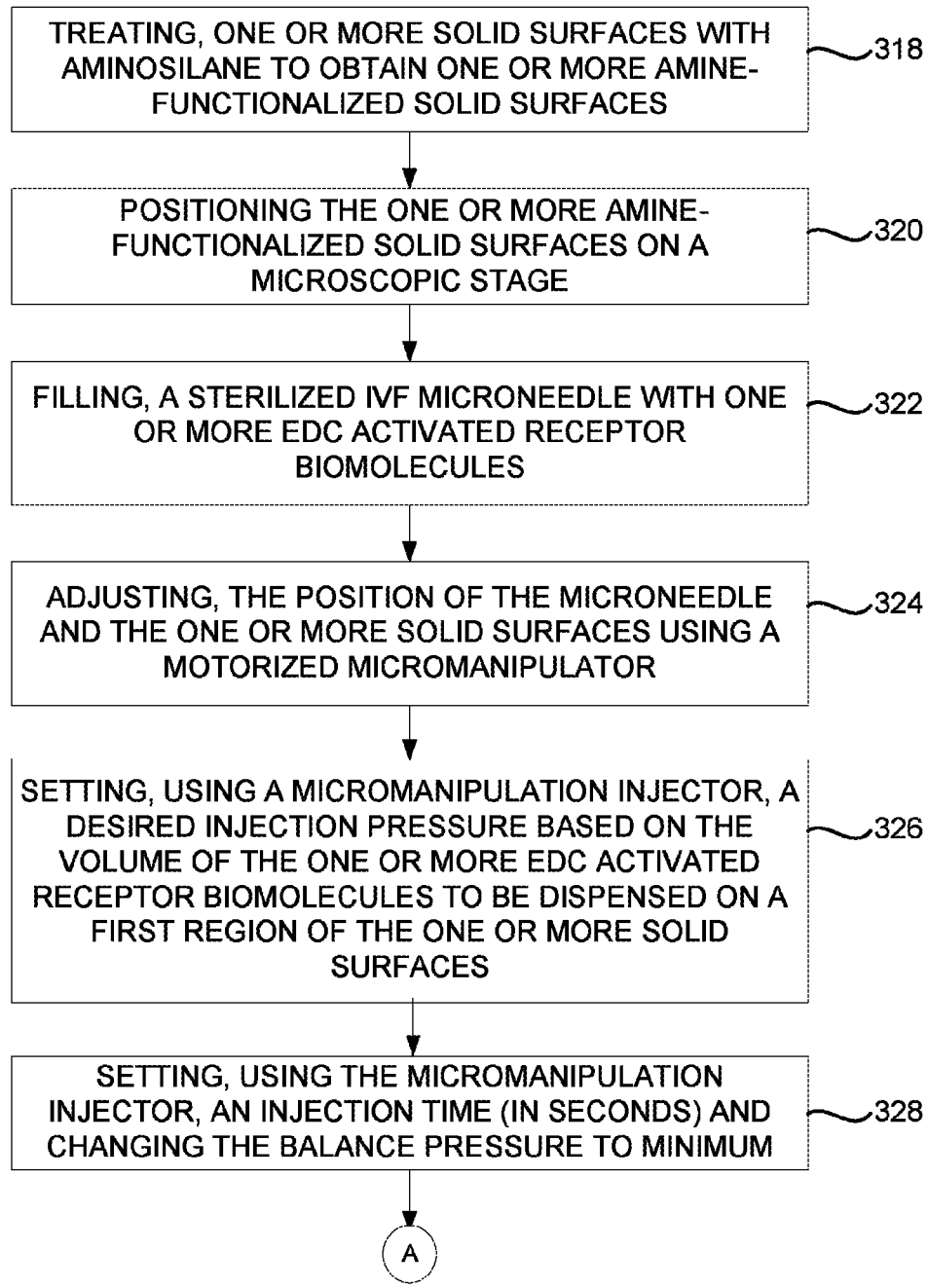
FIGS. 3B and 3C are flow diagrams illustrating an asymmetric immobilization process of immobilizing one or more receptor biomolecules on one or more solid surfaces using a micromanipulation injector according to an embodiment herein.
Figure 3C:
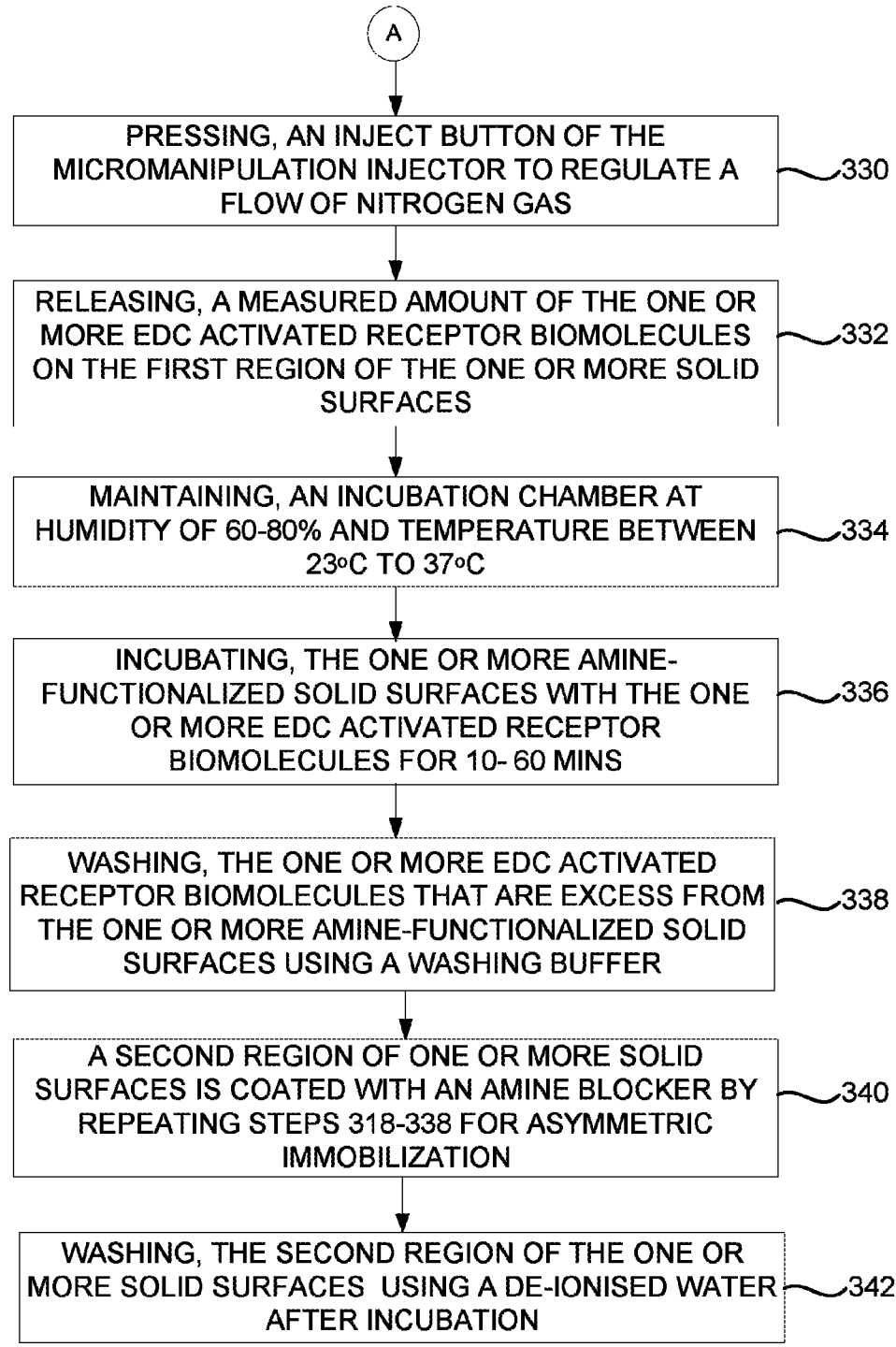

FIGS. 3B and 3C are flow diagrams illustrating an asymmetric immobilization process of immobilizing one or more receptor biomolecules on one or more solid surfaces using a micromanipulation injector according to an embodiment herein. At step 318, the one or more solid surfaces are treated with aminosilane to obtain one or more amine-functionalized solid surfaces. At step 320, the one or more amine-functionalized solid surfaces are positioned on a microscopic stage. At step 322, a sterilized IVF microneedle of the micromanipulation injector is filled with one or more EDC activated receptor biomolecules. At step 324, the position of the microneedle and the one or more solid surfaces are adjusted using a motorized micromanipulator. At step 326, a desired injection pressure is set using the micromanipulation injector based on the volume of the one or more EDC activated receptor biomolecules to be dispensed (e.g., in femtoliters to microliters) on a first region of the one or more solid surfaces. At step 328, an injection time (in seconds) to inject the one or more EDC activated receptor biomolecules on the first region of the one or more solid surfaces is set using the micromanipulation injector, and the balance pressure of the micromanipulation injector is changed to minimum. At step 330, an inject button of the micromanipulation injector is pressed to regulate a flow of nitrogen gas. At step 332, a measured amount of the one or more EDC activated receptor biomolecules is released on the first region of the one or more solid surfaces. At step 334, an incubation chamber is maintained at humidity of 60-80% and temperature between 23° C. to 37° C. At step 336, the one or more amine-functionalized solid surfaces are incubated with the one or more EDC activated receptor biomolecules for 10-60 mins. At step 338, the one or more EDC activated receptor biomolecules that are excess is washed from the one or more amine-functionalized solid surfaces using a washing buffer. At step 340, a second region of one or more solid surfaces is coated with an amine blocker by repeating steps 318-338 for asymmetric immobilization. At step 342, the second region of the one or more solid surfaces is washed using a de-ionised water after incubation.

Figure 4A:
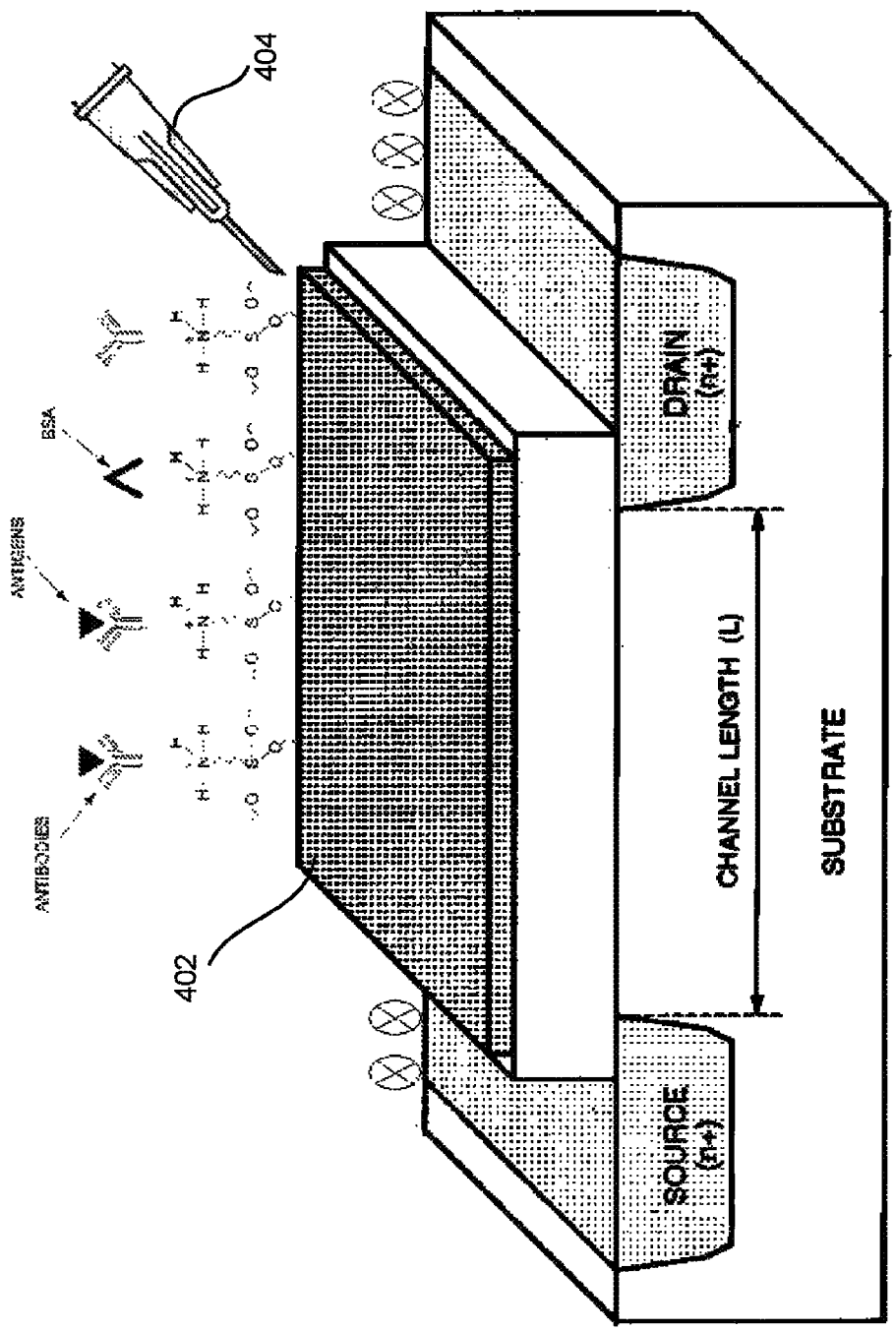
FIG. 4A illustrates a schematic view of a field effect transistor based biosensor that is immobilized with one or more site-specific oriented bioreceptor molecules the asymmetric immobilization process of FIG. 3A according to an embodiment herein.

FIG. 4A illustrates a schematic view of a field effect transistor based biosensor that is immobilized with one or more site-specific oriented bioreceptor molecules the asymmetric immobilization process of FIG. 3A according to an embodiment herein. The field effect transistor based biosensor includes a Field effect transistor (FET) gate, a reference electrode, a source, and a drain. The FET gate is immobilized with one or more site-specific oriented bioreceptor molecules using a micromanipulation injector 404. When the immobilized FET gate is exposed to an analyte biomolecule, the gate charge distribution changes due to binding of analyte molecule with the one or more site-specific oriented bioreceptor molecules, which results in a change in the conductance of the FET channel. The reference electrode may be coated with an amine blocker depending on the proximity with FET gate. The source and drain is coated with the amine blocker to prevent from any biological interaction. When the analyte biomolecule binds to the one or more site-specific oriented bioreceptor molecules, a change in the surface charge density of the FET gate occurs. The change the surface charge density alters the potential in the semiconductor, and the conductivity in the channel of the field-effect transistor. In one embodiment, the interaction of the analyte biomolecule and one or more site-specific oriented bioreceptor molecules may take place at the Angstrom length scale. The field effect transistor based biosensor may be used for on-line monitoring in medical diagnostics, biological research, environmental protection, and food analysis. The field effect transistor based biosensor is made up of a sensor and a measurement circuit. The field effect transistor based biosensor is compact, low weight, low cost, and compatible with commercial planar processes for large-scale circuitry. The field effect transistor based biosensor minimizes the usage of expensive reagent.

Figure 4B:
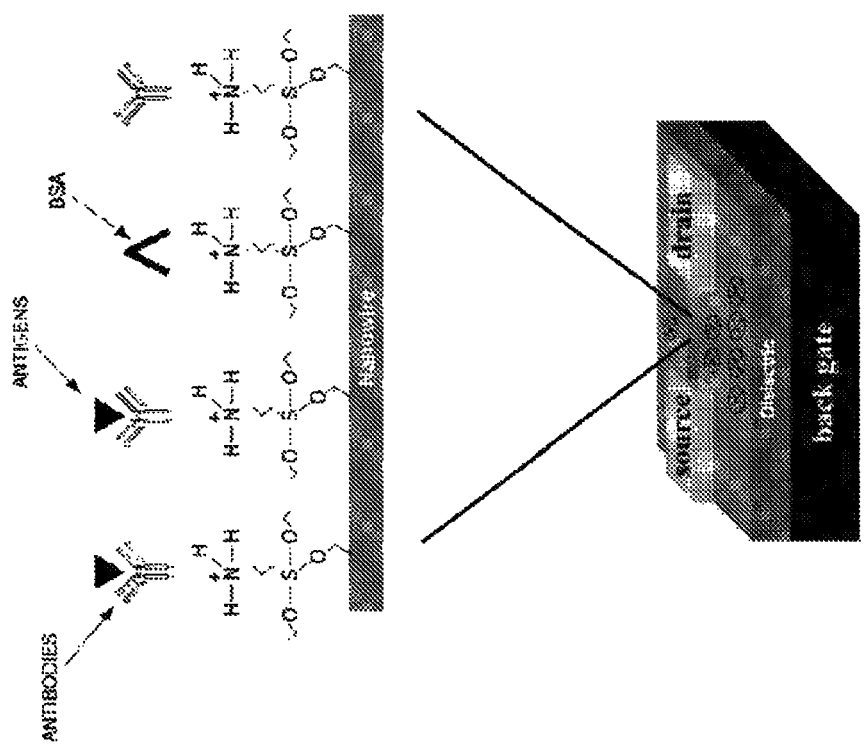
FIG. 4B illustrates a schematic view of a nanowire transistor that are immobilized with one or more site-specific oriented bioreceptor molecules using the asymmetric immobilization process of FIG. 3A according to an embodiment herein.

FIG. 4B illustrates a schematic view of a nanowire transistor that are immobilized with one or more site-specific oriented bioreceptor molecules using the asymmetric immobilization process of FIG. 3A according to an embodiment herein. The nanowire transistor configured as biosensor includes a gate, a source, and a drain. The gate is immobilized with one or more site-specific oriented bioreceptor molecules using a micromanipulation injector. When the immobilized gate is exposed to an analyte biomolecule, the gate charge distribution changes due to binding of analyte molecule with the one or more site-specific oriented bioreceptor molecules, which results in increase in the conductance of the nanowire transistor channel. The source and drain is coated with the amine blocker to prevent from any biological interaction. When the analyte biomolecule binds to the one or more site-specific oriented bioreceptor molecules, a change in the surface charge density of the gate occurs. The change the surface charge density alters the potential in the semiconductor, and increases the conductivity in the channel of the nanowire transistor.

The asymmetric immobilization process eliminates the problems associated due to stiction and the fragile nature (i.e. Temperature sensitive and hygroscopic condition) of the one or more receptor biomolecules with covalent linkage to one or more solid surfaces. The asymmetric immobilization process eliminates leaching and distortion of the one or more receptor biomolecules structure while immobilizing on the one or more solid surfaces. The asymmetric immobilization process of immobilizing the one or more receptor biomolecules on the one or more solid surfaces consumes less time. The importance of using EDC as a crosslinker leads to site-specific orientation of the one or more receptor biomolecules onto the one or more solid surfaces, which places the analyte biomolecule binding site facing away from the one or more solid surfaces. As a result, 2.7 fold higher analyte biomolecule binding capacity is attained than randomized coupling reaction. The asymmetric immobilization process improves distribution of the one or more receptor biomolecules/Antibody on the one or more solid surfaces (microcantilever). The asymmetric immobilization process may be used for immunoassays, enzyme-linked immunosorbent assays (ELISA), surface plasmon resonance immunoassays, and microarrays or microfluidic assays. The asymmetric immobilization process may be used for immobilizing enzyme for analytical use in fermentation and food industry, continuous monitoring of biosensing device, protein array chips, screening techniques, immunoaffinity process, genomic/DNA microarray, and therapeutic use in Point-of-Care or diagnostic kits. In one embodiment, the one or more receptor molecules are coated on the one or more solid surfaces using IVF embryo micromanipulation injector, in femto to picoliter volumes.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

We claim:

1. An asymmetric immobilization process that immobilizes a plurality of receptor biomolecules on a plurality of micro-cantilevers comprising:
    activating the plurality of micro-cantilevers using an oxidizing agent;
    treating the plurality of micro-cantilevers with aminosilane to obtain a plurality of amine functionalized micro-cantilevers;
    treating the plurality of receptor biomolecules with a 1-Ethyl-3-(3-dimethylaminopropyl)carbodiimide (EDC) to obtain a plurality of site-specific EDC activated receptor biomolecules;
    immobilizing the plurality of site-specific EDC activated receptor biomolecules on a first layer of the plurality of amine functionalized micro-cantilevers, wherein the immobilizing comprises treating the plurality of site-specific EDC activated receptor biomolecules with amine groups of the first layer of the plurality of amine functionalized micro-cantilevers to form a covalent amide bond, wherein the EDC is hydrolyzed from the plurality of site-specific EDC activated receptor biomolecules when the plurality of site-specific EDC activated receptor biomolecules binds with amine groups of the plurality of amine functionalized micro-cantilevers;
    coating a second layer of the plurality of amine functionalized micro-cantilevers with at least one of (a) acyl chloride, and (b) anhydrides; and
    treating the first layer of the plurality of amine functionalized micro-cantilevers with bovine serum albumin to block unbound amine groups of the plurality of amine functionalized micro-cantilevers.

2. The asymmetric immobilization process as claimed in claim 1, wherein the acyl chloride is selected from a group consisting of:
    (i) formyl chloride (CHClO);
    (ii) ethanoyl chloride (C2H3ClO);
    (iii) propanoyl chloride (C3H5ClO);
    (iv) butanoyl chloride (C4H7ClO); and
    (v) octanoyl chloride (C8H15ClO).

3. An asymmetric immobilization process that immobilizes a plurality of receptor biomolecules on a plurality of micro-cantilevers comprising:
    activating the plurality of micro-cantilevers using an oxidizing agent;
    treating the plurality of micro-cantilevers with aminosilane to obtain a plurality of amine functionalized micro-cantilevers;
    washing the plurality or amine functionalized micro-cantilevers using organic solvents;
    treating the plurality of receptor biomolecules with a 1-Ethyl-3-(3-dimethylaminopropyl)carbodiimide (EDC) to obtain a plurality of site-specific EDC activated receptor biomolecules;
    immobilizing the plurality of site-specific EDC activated receptor biomolecules on a first layer of the plurality of amine functionalized micro-cantilevers, wherein the immobilizing comprises treating the plurality of site-specific EDC activated receptor biomolecules with amine groups of the first layer of the plurality of amine functionalized micro-cantilevers to form a covalent amide bond, wherein the EDC is hydrolyzed from the plurality of site-specific EDC activated receptor biomolecules when the plurality of site-specific EDC activated receptor biomolecules binds with amine groups of the plurality of amine functionalized micro-cantilevers;
    coating a second layer of the plurality of amine functionalized micro-cantilevers with least one of (a) acyl chloride, and (b) anhydrides;
    washing the plurality of site-specific EDC activated receptor biomolecules that are excess from the plurality of amine functionalized micro-cantilevers using at least one of (a) a phosphate buffer saline, (b) de-ionised water; and
    treating the first layer of the plurality of amine functionalized micro-cantilevers with bovine serum albumin to block unbound amine groups of the plurality of amine functionalized micro-cantilevers.

4. The asymmetric immobilization process as claimed in claim 3, wherein the plurality of receptor biomolecules is selected from a group consisting of:
    (i) an anti-myoglobin antibody;
    (ii) an anti-FABP3 antibody;
    (iii) an anti-troponin antibody;
    (iv) an anti-Human IgG antibody;
    (v) an anti-IMA Antibody;
    (vi) an anti-Myeloperoxidase (MPO) Antibody;
    (vii) an anti-Glycogen Phosphorylase Isoenzyme BB- (GPBB) Antibody;
    (viii) an anti-Serum creatinine antibody;
    (ix) an anti-Serum cystatin C antibody;
    (x) an anti-Urine albumin antibody;
    (xi) an anti-Neutrophil gelatinase-associated lipocalin (NGAL) antibody;
    (xii) an anti-Kidney injury molecule 1 (KIM-1) antibody;
    (xiii) an anti-Liver-type fatty acid-binding protein (L-FABP) antibody;
    (xiv) an anti-Interleukin 18 (IL-18), β-trace protein (BTP) antibody;
    (xv) an anti-Aasymmetric dimethylarginine (ADMA) antibody; and
    (xvi) an anti-Urine cystatin C antibody.

* * * * *